(12) United States Patent
Howley et al.

(10) Patent No.: US 6,924,137 B2
(45) Date of Patent: Aug. 2, 2005

(54) METHOD FOR VIRUS PROPAGATION

(75) Inventors: Paul Howley, Martinsried (DE); Karl Heller, Unterföhring (DE); Ingmar Räthe, München (DE)

(73) Assignee: Bavarian Nordic A/S, Copenhagen S (DK)

( * ) Notice: Subject to any disclaimer, the term of this patent is extended or adjusted under 35 U.S.C. 154(b) by 0 days.

(21) Appl. No.: 10/483,707

(22) PCT Filed: Jul. 2, 2002

(86) PCT No.: PCT/EP02/07280
§ 371 (c)(1),
(2), (4) Date: Feb. 17, 2004

(87) PCT Pub. No.: WO03/008533
PCT Pub. Date: Jan. 30, 2003

(65) Prior Publication Data
US 2004/0234950 A1 Nov. 25, 2004

(30) Foreign Application Priority Data
Jul. 18, 2001 (DK) .................................. 2001 01122

(51) Int. Cl.$^7$ .............................. C12N 7/01; C12N 7/02
(52) U.S. Cl. ................................... 435/235.1; 435/239
(58) Field of Search ............................ 435/235.1, 239, 435/320.1; 424/199.1, 93.2

(56) References Cited

U.S. PATENT DOCUMENTS

| | | | |
|---|---|---|---|
| 4,567,147 A | | 1/1986 | Ooi et al. |
| 5,616,487 A | | 4/1997 | Palsson et al. |
| 5,993,824 A | * | 11/1999 | Murphy et al. ........... 424/211.1 |
| 6,761,893 B2 | * | 7/2004 | Chaplin et al. ........... 424/199.1 |

OTHER PUBLICATIONS

Drillien et al (Virology 119:372–381, 1982).*
Perkus et al. (Journal of Leukocyte Biology 58:1–13, 1995).*

Slonim D et al "Reaction of Infectious and lethal activities of three strains of vaccinia virus to the Incubation temperature"; *Journal of Hygiene, Epidemiology, Microbiology and Immunology*; vol. 10, pp. 480 to 485 (1972).

Slonim D et al "Influence of the Incubation temperature on the dynamics of reproduction and plaque formation of three strains of vaccinia virus in cell cultures"; *Journal of Hygiene, Epidemiology, Microbiology and Immunology*; vol. 16, pp 474 to 479 (1972).

Slonim D et al "Reproduction in chick chorioallantoic membrane and lethal effect in chick embryos of three strains of vaccinia virus in relation to the Incubation temperature"; *Journal of Hygiene, Epidemiology, Microbiology and Immunology*; vol. 17, pp 21 through 25 (1973).

Fuchs N et al "Virus Isolation and titration at 33° C and 37° C"; Med. Microbiol. Immunol.; 161, pp 123 to 126 (1975).

Mingle, Julius A.A. et al "Maintenance of primary african green monkey kidney (pAGMK) and vero cells at room temperature (25° C). A system for virus isolation in community practice"; *Can. J Microbiol.*; vol. 20, pp 391 to 397 (1974).

Sutter, Gerd et al "Nonreplicating vaccinia vector efficiently expresses recombinant genes"; *Proc. Nat. Acad. Sci. USA*; vol. 89, pp 10847 to 10851 (Nov. 1992).

Sugimoto, Masanobu et al "Characteristics of an attenuated vaccinia virus strain LC16mO, and its recombinant virus vaccines"; *Vaccine 1994*; vol. 12, No. 8, pp 675 to 681.

* cited by examiner

Primary Examiner—Mary E. Mosher
(74) Attorney, Agent, or Firm—Herbert Dubno; Jonathan Myers

(57) ABSTRACT

The present invention relates to a process for producing poxvirus, in particular Chordopoxvirus, wherein the poxvirus is cultivated at a temperature below 37° C. The process leads to increased virus propagation at the decreased temperature.

28 Claims, 5 Drawing Sheets

METHOD FOR VIRUS PROPAGATION

CROSS REFERENCE TO RELATED APPLICATION

Figure 1:
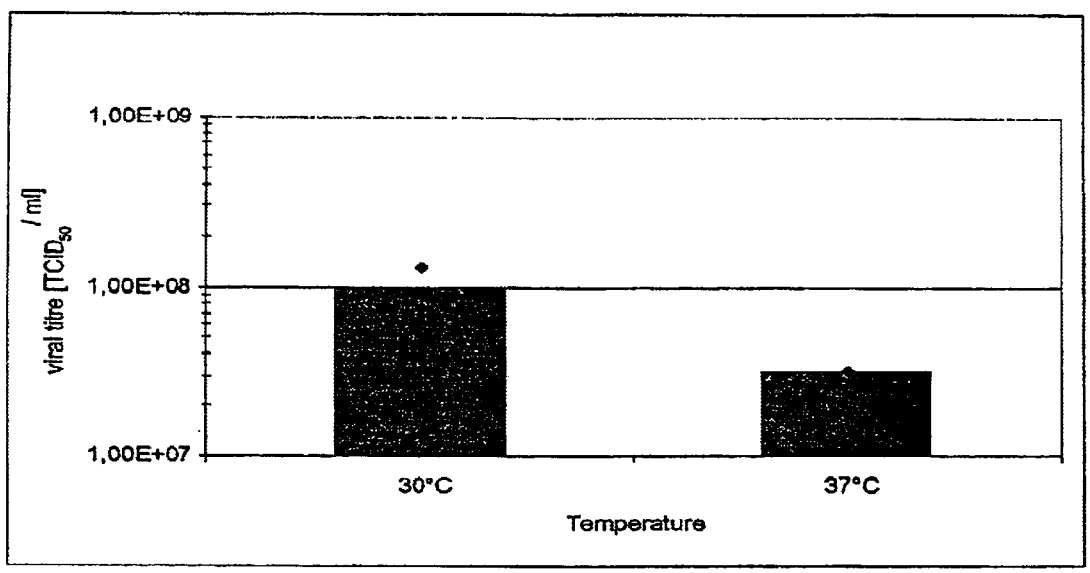

The present application is the U.S. National Phase of PCT/EP02/07280 filed 2 Jul. 2002 which claims the benefit of the filing date of 18 Jul. 2001 of Danish Patent Application PA 2001 01122.

The present invention relates to a process for producing poxvirus, in particular Chordopoxvirus, wherein the poxvirus is cultivated at a temperature below 37° C. The process leads to increased virus propagation at the decreased temperature.

BACKGROUND OF THE INVENTION

The poxviridae comprise a large family of complex DNA viruses that replicate in the cytoplasm of vertebrate and invertebrate cells. The family of poxviridae can be divided into the subfamily chordopoxvirinae (vertebrate poxviruses) and entomopoxvirinae (insect poxviruses) (Fields Virology/eds.: Fields, B. N., Knipe, D. M., Howley, P. M.; $3^{rd}$ ed/ISBN 0-7817-0253-4/ see in particular chapter 83).

The chordopoxvirinae comprise numerous animal poxviruses (classified in different genera), such as camelpox-viruses, sheeppox-virus, goatpox-virus or Avipoxviruses, in particular fowlpoxvirus and also poxvirusus that are of relevance for humans such as the variola virus and the vaccinia virus.

Pox-viruses, in particular chordopoxvirinae, are important pathogens in humans and animals. There is also a long history of vaccination against pox-virus infections. Nearly two centuries ago, humans were prophylactically inoculated with cowpox to immunise them against smallpox. Later immunisation was performed with the Vaccinia virus. However, smallpox vaccination with this Vaccinia virus resulted occasionally in serious complications, such as post-vaccinal encephalitis, generalised Vaccinia or contact infection. Then, a new vaccine that does not show these complications, was developed by Anton Mayr. The pox vaccine consists of the poxvirus Modified Vaccinia Virus Ankara (MVA) and was used for vaccination against smallpox in about 150 000 vaccinations without causing any complications related to the vaccination. Even children with immunologic deficiencies did not show serious side effects. The MVA was obtained by mutation and selection of the original vaccinia virus Ankara after 575 passages in chicken embryo fibroblast cultures. The safety of this MVA is reflected by biological, chemical and physical characteristics. MVA has a reduced molecular weight, six deletions in the genome, and is highly attenuated for mammalian cells, i.e., DNA and protein is synthesised but virtually no viral particles are produced.

The vaccination against smallpox was highly successful. In 1979, the World Health Organisation declared the eradication of smallpox. Accordingly, the mass vaccination of children was discontinued and only laboratory workers and members of the armed forces of some countries are vaccinated.

With the eradication of smallpox, the predominant cause of pox viral infection in humans was removed. However, some non-human poxviruses have reduced host specificity, i.e., they cause infections not only in their typical host (e.g. for cowpox the cow), but also in other animals, (e.g. rats and cats). Humans can be infected by this route as well. Since parts of the population are no longer immune against smallpox, poxvirus infections of animal species can be dangerous for them. Domestic animals are the main source of infection for humans. Accordingly, the vaccination of domestic animals against poxviruses is. of increasing importance. In addition, poxviruses are important vectors for the expression of foreign genes for example for use as a vaccine or for gene therapy, i.e. to transfer nucleic acid sequences into a target cell where they are expressed. Consequently, an efficient and cost effective production method for poxviruses is required.

Poxviruses can be amplified in different cell types. For example, chordopoxvirinae, in particular MVA are amplified in cell cultures of primary or secondary chicken embryo fibroblasts (CEF). The cells are obtained from embryos of chicken eggs that are incubated for 10 to 12 days. The cells of the embryos are then dissociated and purified. These primary CEF cells can either be used directly or after one further cell passage as secondary CEF cells. Subsequently, the primary or secondary CEF cells are infected with the MVA. For the amplification of MVA the infected cells are incubated for 2–3 days at 37° C. (see, e.g., Meyer, H. et al. 1991; J. of General Virology 72, 1031–1038; Sutter et al. 1994, Vaccine, Vol. 12, No. 11, 1032–1040). Although other chordopoxviruses are amplified in different cell types, the same temperature of 37° C. is chosen in those cases. For example, the Vaccinia virus obtainable from ATCC (No. VR1354), which is cultivated in HeLa S3 cells (human cervix carcinoma cells) is also incubated for 3 days at 37° C. (Current protocols in molecular biology 1998, Chapter 16, Unit 16.16, John Wiley & Sons, Inc). Furthermore, the MVA adapted for growing in Vero cells (monkey kidney cells) is also amplified at 37° C. (PCT/EP01/02703). Consequently, independent from the cells used for amplification and independent form the species or strain of the chordopoxvirus, amplification of the viruses is performed at 37° C. This selected temperature corresponds well with the general knowledge of the skilled practitioner: Pox-viruses nearly exclusively amplified in the laboratories are obtained from warm-blooded animals with a body temperature of approximately 37° C. Since chordopoxviruses are adapted for growing in said animals, they are adapted for growing at 37° C., i.e. they should amplify most efficiently at 37° C.

Because of similar reasons Entomopoxviruses are cultivated at temperatures lower than 37° C.: The body temperature of insects is significantly lower than 37° C. and depends to a larger extent on the temperature of the environment. Thus, in contrast to Chordopoxviruses the Entomopoxviruses are adapted for growing at lower temperatures. U.S. Pat. No. 5,721,352 and U.S. Pat. No. 5,174,993 disclose an optimal temperature for growth of the Entomopoxvirus species *Amsacta moorei* Entomopoxvirus (AmEPV) of 28° C. in the laboratory. However, these patents do not disclose the cultivation of Chordopoxviruses under these temperature conditions.

Furthermore, production of vaccines against other viral infections is in general performed at 37° C. Only some measles vaccines are produced at a lower temperature. In this case, a measles vaccine, which was originally produced at 37° C. and which frequently caused severe side effects, was attenuated by continuous passaging of the virus at 32° C. After 85 passages of the strain at 32° C. the strain was attenuated, i.e. the disease-causing capacity of the virus was considerably reduced (Plotkin, Orenstein: Vaccines, $3^{rd}$ edition, 230–232). In conclusion, viruses of warm-blooded animals and particularly Vaccinia viruses are expected to amplify most efficiently at 37° C., since they are found in animals with said body temperature and adaptation to a lower temperature is only achieved after multiple passages at said lower temperature. Furthermore, adaptation to a lower temperature is associated with attenuation and therefore often with reduced reproduction capacity of the virus.

U.S. Pat. No. 5,616,487 discloses a process for producing a stabilized virus, in particular a stabilized retrovirus, by culturing virus producing cells with a stabilizing agent at a temperature below 37° C. The stabilizing agents are lipids or surfactants. The patent specifically discloses Pluronic F-68 and Lipid Concentrate as stabilizing agents. Lipid Concentrate is said to contain cholesterol, cod liver oil, Pluronic F-68, d-alpha-tocopherol acetate and Tween 80. In an alternative embodiment U.S. Pat. No. 5,616,487 discloses a process for cultivating specific retrovirus producing cells at a temperature of lower than 37° C., wherein the produced retrovirus is stabilized using a stabilizer as defined above.

OBJECT OF THE INVENTION

It was an object of the present invention to provide a method for preparing pox-viruses, in particular Chordopoxviruses which leads to a higher yield of virus particles per infected cell.

DETAILED DESCRIPTION OF THE INVENTION

Said object is achieved by a process for preparing poxvirus, in particular a Chordopoxvirus, wherein the virus producing cells are cultivated at a temperature below 37° C.

It was surprisingly found that the method according to the invention leads to much more efficient amplification of the virus at the lower temperature (below 37° C.) which in turn results in a higher virus yield relative to the number of infected cells. Consequently, fewer cells are required to produce the same amount of virus. This is especially advantageous for modified Vaccinia Virus Ankara (MVA), since the production of CEF cells required for MVA amplification is laborious and expensive. Furthermore, the reduction of the incubation temperature allows saving energy during the amplification process of the poxvirus and hence saves costs in the production of the viruses.

The term "poxvirus" as used in the present application refers preferably to poxviruses of the subfamily Chordopoxvirinae (vertebrate poxviruses) (Fields Virology/eds.: Fields, B. N., Knipe, D. M., Howley, P. M.; $3^{rd}$ ed/ISBN 0-7817-0253-4/ see in particular chapter 83). The terms "Chordopoxviruses", "Chordopoxvirinae" and "vertebrate poxviruses" are used interchangeably in the present application. Preferred Chordopoxviruses are poxviruses of the genera Orthopoxvirus, Parapoxvirus, Avipoxvirus, Capripoxvirus, Lepripoxvirus, Suipoxvirus, Molluscipoxvirus and Yatapoxvirus. Most preferred are poxviruses of the genera Orthopoxvirus and Avipoxvirus.

In a preferred embodiment the pox-virus being produced by the method according to the present invention is a pox-virus, in particular a chordopoxvirus, which is useful as a vaccine or which can be used as a gene therapeutic vector in order to introduce genes of interest into a host cell. Suitable virus strains are well known to the skilled person. Suitable strains can be obtained e.g. from the American Type Culture Collection (ATCC) or the European Collection of Animal Cell Cultures (ECACC).

As mentioned above, particularly preferred pox-viruses for being produced according to the present method are Avipoxviruses and orthopoxviruses. Examples for orthopoxviruses are vaccinia viruses; such a the Vacciniavirus strains Elstree, Western Reserve, Wyeth, NYVAC, NYCBOH, Paris, Copenhagen, more preferably the various MVA strains and most preferably MVA-BN, deposited at the ECACC under V00083008 or derivatives thereof. MVA-BN and its derivatives have been described in detail in the PCT application PCT/EP01/13628, entitled "Modified Vaccinia Ankara Virus Variant".

A "derivative" of the deposited virus is a virus, which shows essentially the same growth characteristics, in particular the same temperature dependency as the deposited strain but might differ in at least one part of its genome.

The process according to the present invention can be carried out with wild-type viruses, attenuated viruses and recombinant viruses, respectively.

An "attenuated virus" is a virus originating from a pathogenic virus but that upon infection of the host organism leads to a lower mortality and/or morbidity compared to the non-attenuated parent virus. Examples of attenuated poxviruses are known to the person skilled in the art. An example for an attenuated Vaccinia virus is strain MVA, in particular the strain that has been deposited at ECACC with the deposition number V00083008 (see above).

The term "recombinant virus" refers to any virus having inserted into the viral genome a heterologous gene that is not naturally part of the viral genome. A heterologous gene can be a therapeutic gene, a gene coding for a peptide comprising at least one epitope to induce an immune response, an antisense expression cassette or a ribozyme gene. Methods to construct recombinant viruses are known to a person skilled in the art. The most preferred poxvirus vector is MVA, in particular MVA 575 and MVA-BN (see above).

In contrast to all previous teachings in the prior art the inventors of the present invention found that out of six temperatures between 26° C. and 37° C. the pox-viruses, in particular Chordopoxviruses, amplified the least efficient at an incubation (cultivation) temperature of 37° C. It was surprisingly found that a method for the amplification of pox-virus, in particular Chordopoxvirus, leads to higher yields of virus if the virus producing cells are cultivated at a temperature below 37° C., preferably between 36.5° C. and 26° C. or between about 26° C. and about 36° C., more preferably between 28° C. and 33° C., even more preferably between 28° C. and 32° C., most preferably at 30° C.

Another preferred temperature range is 30° C. to 36.5° C. Particularly good results have been obtained in the subranges 30° C. to 35° C., 30° C. to 33° C. and 30° C. to 32° C. The most preferred temperature is 30° C.

The term "about" in connection with temperature values refers preferably to the specifically mentioned temperatures and to temperatures being up to 0.5° C. higher or lower than the specifically mentioned temperatures. By way of example a temperature of "about 30° C. is to be interpreted as a temperature in the range of 29.5° C. to 30.5° C.

In more general terms, in the process according to the present invention the respective poxvirus is produced by cultivation of an infected cell at a temperature which is lower than the body temperature of the animal, including an human, that is the natural host of the respective poxvirus. As far as Vacciniavirus is concerned buffaloes are regarded as natural host (Baxby, D.: Jenner's smallpox vaccine: the riddle of vaccinia virus and its origin. London: Heinemann Educational; 1981: 1–214).

The cultivation of virus producing cells is preferably performed for at least 24 hours, more preferably for at least 2 days or for at least 3 days. Normally, virus free cells are grown at 37° C. until a sufficient amount of cells is obtained.

Then the cell culture is inoculated with virus and the temperature is then reduced to the above-indicated temperature. In an alternative embodiment the cell culture is brought to the above temperature before being inoculated with virus.

The media used for the cultivation of the cells before infection and for the production of virus using the process according to the present invention may be the same or different. All media are conventional standard media known to the person skilled in the art. If necessary it is possible to add further additives such as antibiotics, additional amino acids and/or foetal calf serum.

According to a preferred embodiment the media used in the process according to the present invention do not contain lipids or surfactants to stabilize the viral lipid envelope. More preferably, the media used in the process according to the present invention do not contain any of the following stabilizing agents: Pluronic F-68, the combination of Pluronic F-68 and Tween 80™ or Lipid Concentrate (Gibco/BRL, Gaithersburg, Md., catalogue no: 21900-014) that contains cholesterol, cod liver oil, Pluronic F-68, d-alpha-tocopherol acetate and Tween 80.

For the Chordopoxviruses cells are known to the person skilled in the art that can be used in the process according to the present invention. The type and nature of the cells is not critical as long as the cells can be infected with the respective virus and as long as progeny virus is produced from the infected cells. Preferably the multiplicity of infection should be lower than 1.

Particularly preferred cells are vertebrate cells, e.g. mammalian or avian cells.

According to a preferred embodiment the vertebrate cells that can be used in the method according to the present invention for Vaccinia viruses, in particular for the Vaccinia virus strains Elstree and MVA, are Chicken Embryo Fibroblasts (CEF). It was particularly unexpected that the process according to the present invention can be used for CEF cells since chicken have a normal average body temperature of 41° C. Thus, the temperatures used according to the present invention of below 37° C., preferably of between 36.5° C. and 26° C., more preferably of between 28° C. and 33° C., even more preferably of between 28° C. and 32° C., most preferably of 30° C. are so different from the normal body temperature of the chicken that one would have assumed that these cells can not be used for the propagation of vaccinia viruses at these temperatures. The same considerations apply for temperatures in the range of 30° C. to 36.5° C., 30° C. to 33° C., 30° C. to 32° C., and in particular for the temperature of 30° C.

Moreover, the process according to the present invention is preferably performed in stationary flasks.

A further advantage is that the process leads to increased yields with "normal" virus strains, which do not require a temperature sensitive mutation or a long and complicated attenuation to the reduced temperature. In other words it is not required to use temperature attenuated or temperature sensitive mutants in order to achieve higher yields in virus particles at the lower temperature compared to 37° C.

It is known for temperature attenuated virus or temperature sensitive mutants that they are amplified better at the lower temperature; however, such strains normally are less reproductive than non-attenuated or non-temperature sensitive mutants. Therefore, the big advantage of the method according to the invention lies in the fact that it can be applied to any kind of normal, highly reproductive virus strain.

The virus prepared according to the present invention is preferably used as a vaccine or for preparing a composition used in a gene therapy protocol. Such applications of poxvirus are well established in the art.

SHORT DESCRIPTION OF THE FIGURES

FIG. 1

In FIG. 1 single values from experiment 1 are performed in duplicate (represented as dots). Bars represent the mean values. For single values compare table 1.

FIG. 2

Figure 2:
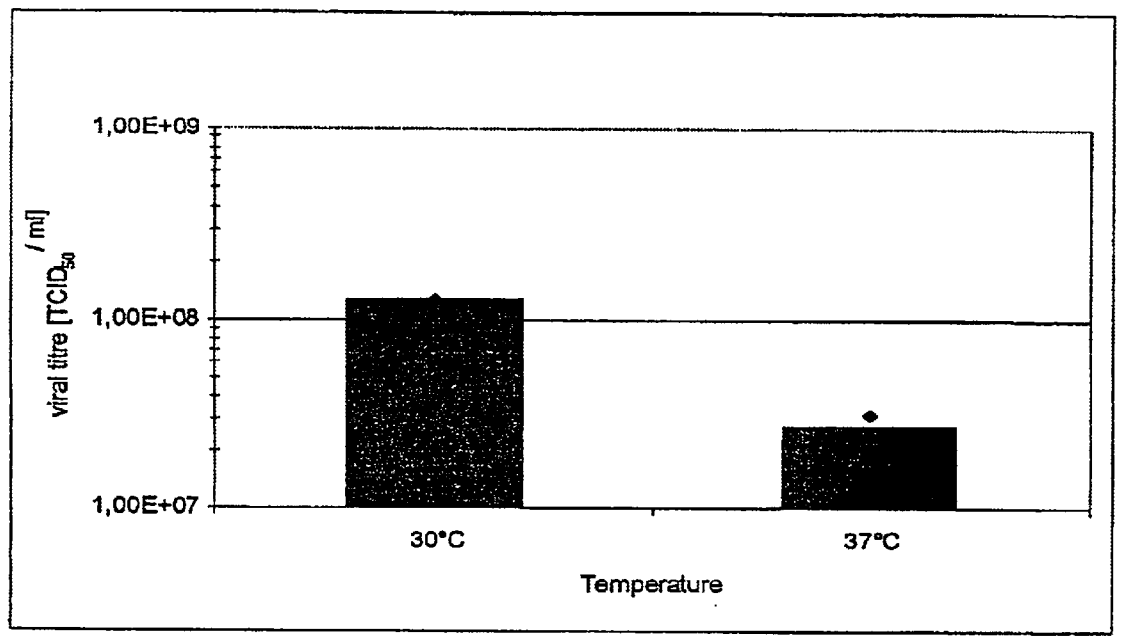

In FIG. 2 single values from experiment 2 are performed in duplicate (represented as dots). Bars represent the mean values. For single values compare table 2.

FIG. 3

Figure 3:
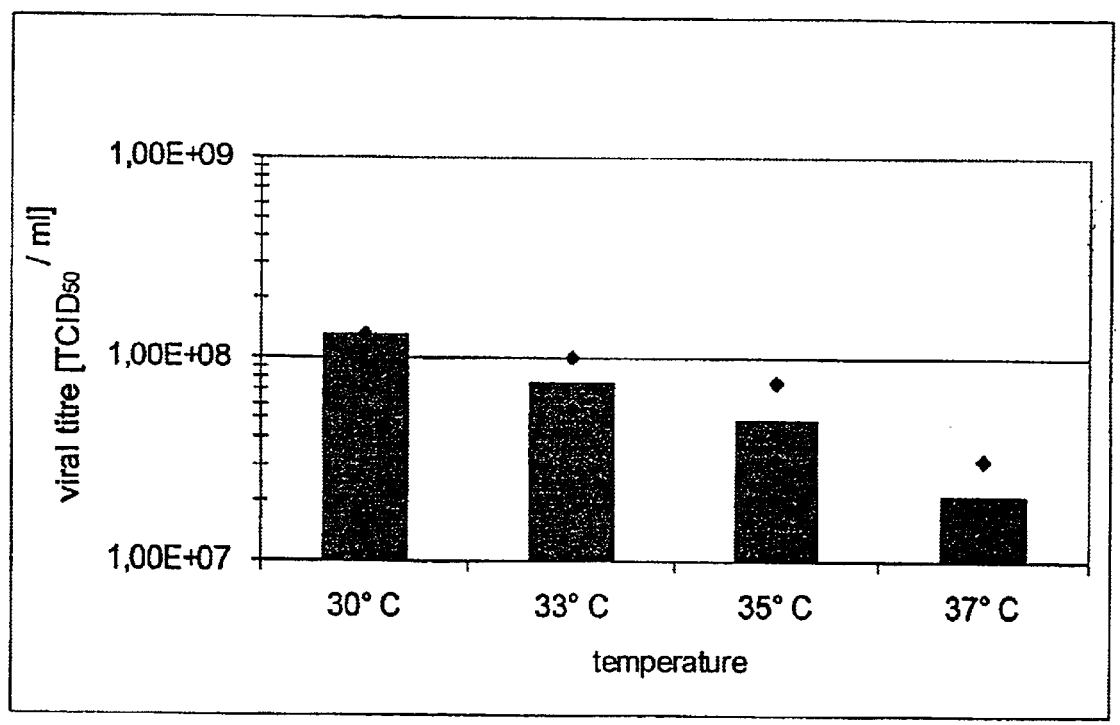

In FIG. 3 dots are single values from the experiments with the four different temperatures (experiment 3) performed in duplicate. Bars represent the mean values. For single values compare table 3.

FIG. 4

Figure 4:
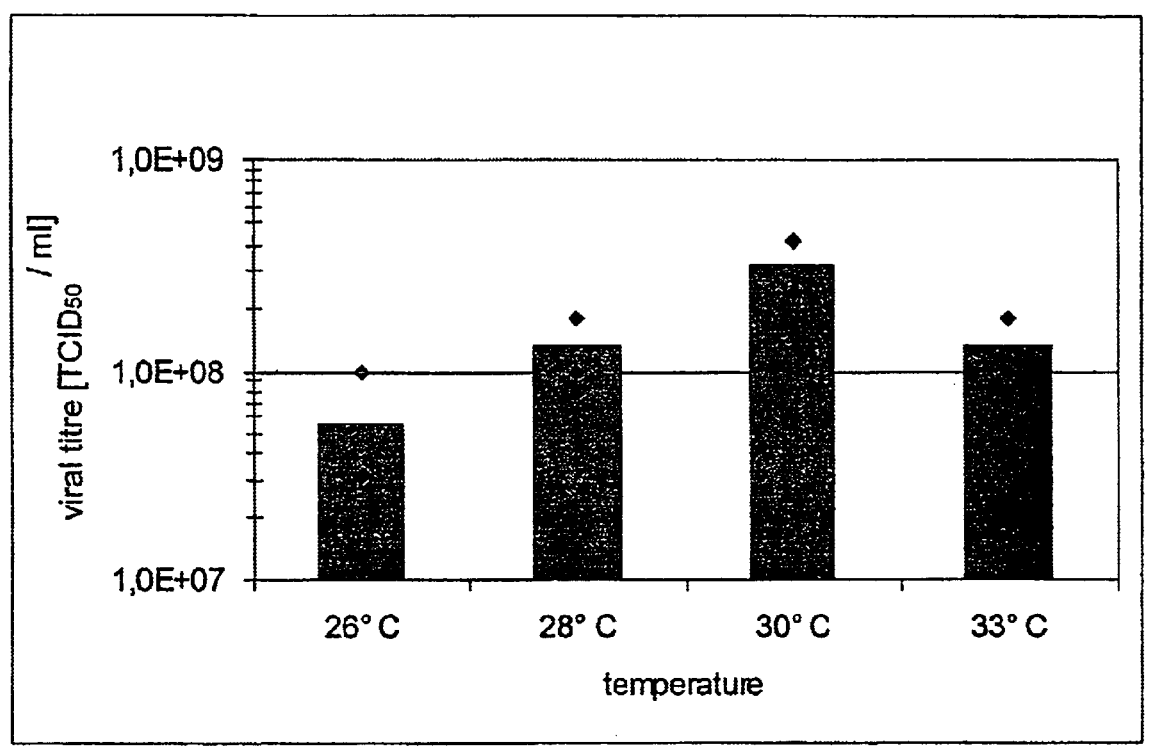

In FIG. 4 dots are single values from the experiments with the four different temperatures (experiment 4) performed in duplicate. Bars represent the mean values. For single values compare table 4.

FIG. 5

Figure 5:
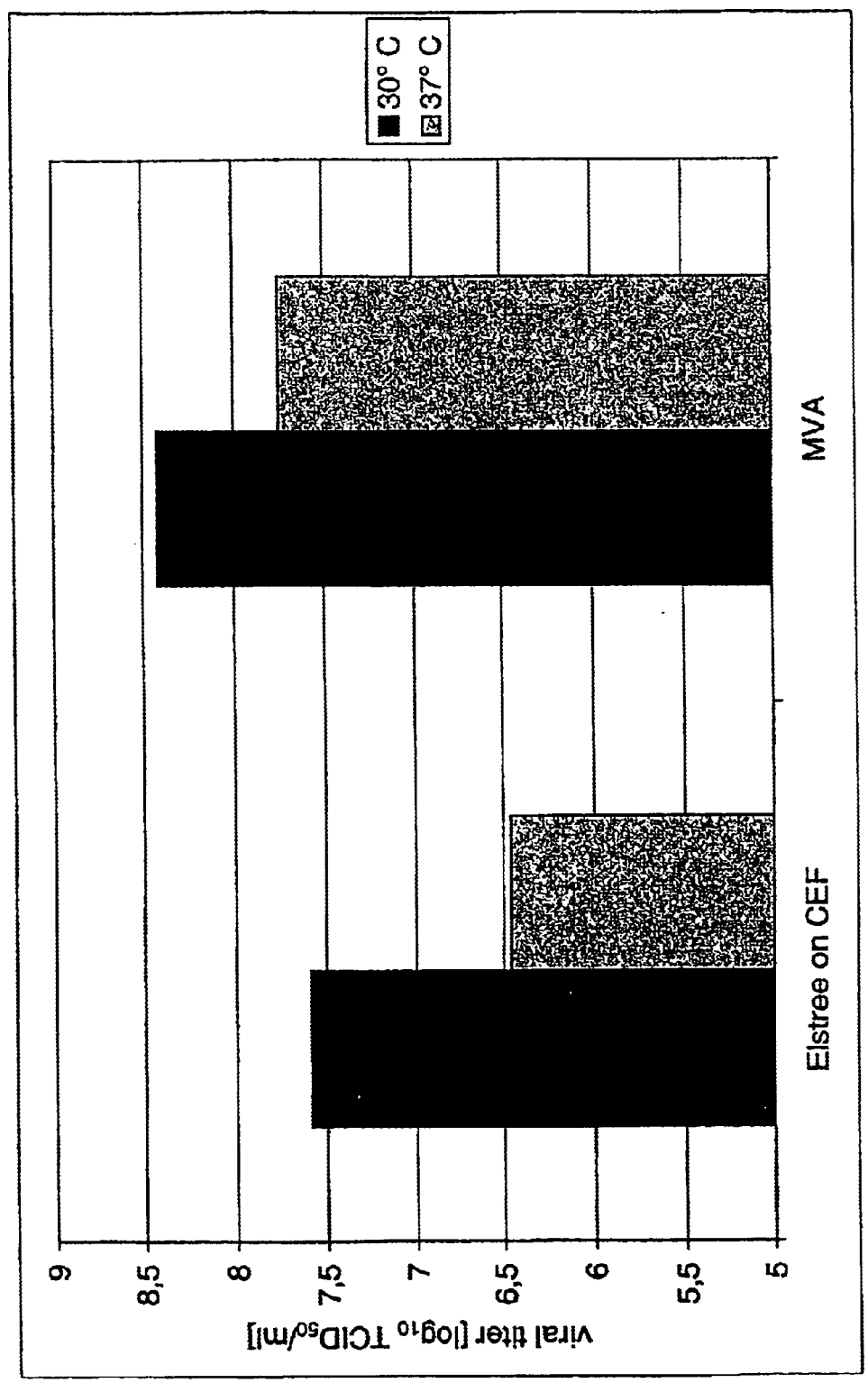

In FIG. 5 bars represent the mean values of the experiments performed in triplicates at 30° C. and 37° C. For single values compare table 5.

SUMMARY OF THE INVENTION

The present invention relates to the following embodiments:

a process of preparing a poxvirus, in particular a Chordopoxvirus, characterized in that the virus is propagated at a cultivation temperature below 37° C.;

the above process characterized in that the virus is propagated at a cultivation temperature of about 26° C. to about 36° C.;

the above process characterized in that the virus is propagated at a cultivation temperature of about 28° C. to about 33° C.;

the above process characterized in that the virus is propagated at a cultivation temperature of about 30° C. to about 33° C.

the above process characterized in that the virus is propagated at a cultivation temperature of about 30° C.;

the above process characterized in that virus propagation is performed for at least 24 hours;

the above process characterized in that virus cultivation is performed for at least 2 to 3 days;

the above process characterized in that the pox-virus is a virus useful as a vaccine or gene therapeutic vector;

the above process characterized in that the pox-virus is selected from the group comprising Avipoxvirus and orthopoxvirus;

the above process characterized in that the virus is a vaccinia virus;

the above process characterized in that the virus is modified vaccinia virus Ankara (MVA), preferably MVA-BN as deposited at ECACC under No. V00083008 or a derivative thereof;

the above process characterized in that it is performed in a stationary flask;

the above process characterized in that the pox-virus is not a temperature sensitive mutant virus;

the above process characterized in that the pox-virus is not a temperature attenuated virus;

the above process characterized in that the virus is propagated in chicken embryo fibroblast cells;

a virus prepared according to any of the above processes;

a composition containing the virus as above;

a vaccine containing the virus as above;

a composition for use in gene therapy comprising a virus genome of the virus prepared according to any of the above processes;

use of a virus prepared according to any of the above processes as a vaccine;

use of a virus proposed according to any of the above processes in gene therapy.

EXAMPLES

The further examples further illustrate the invention.

Example 1

Effect of the Temperature on the Multiplication of MVA

Cell Culture Conditions

Primary CEF-cells were seeded in stationary flasks with a seeding cell density of $2 \times 10^7$ CEF cells/185cm$^2$. Cells were seeded in VP-SFM +4 mM L-Glutamine and 1% Antibiotics/Antimycotics. At day four after seeding a cell density of $5 \times 10^7$ CEF-cells/185 cm$^2$ was assumed. The cells were infected with 0.1 TCID$_{50}$/cell MVA-BN (deposited at ECACC under deposit no. V 00083008) by using RPMI w/o FCS. The infection, followed by incubation for 72 h, was performed at 30° C. and 37° C. (in experiments 1 and 2 with two different CEF preparations), at 30, 33, 35 and 37° C. (experiment 3) and 26, 28, 30 and 33° C. (experiment 4). The experiments were performed in duplicate for each temperature. Virus replication was stopped by scraping the cells into the media and by freezing media and cells together at −20° C. This mixture was freeze/thawed another two times to mechanically release the virus from the cells. For the experiments with 4 different infection temperatures virus replication was stopped by freezing stationary flasks at −20° C. This mixture was freeze/thawed another three times to mechanically release the virus from the cells.

Virus titres from every stationary flask were determined by using an immunohistochemical assay. Infected cells were stained with a Vaccinia virus specific antibody. Secondly, an HRP-coupled antibody directed against the Vaccinia virus antibody was added. After addition of a substrate infected cells appear in blue or brown colour. Evaluation of the assay was done by using the formula of Spearman and Kaerber determining the TCID50/ml (tissue culture infectious dose). Experiments were performed in duplicate. As an acceptance criterion for titration results MVA-BN standard with known titre was used as an internal control for each titration experiment. Results from the experiments were only taken when the values from MVA-BN standard did not differ more-than ±0.5 logs from the overall average.

Results

To include possible growth variations of primary CEF cells, experiments were performed with two different cell preparations when comparing infection temperatures 30° C. and 37° C. The results from the two independent infection experiments are shown in Table 1–2 and FIG. 1–2.

The results of experiments 1 and 2 show a clear increase in the virus yield at 30° C. compared to 37° C. In experiment 1 an increase of 0.5 logs and in experiment 2 of about 0.7 logs was achieved.

TABLE 1

In Table 1 values from experiment 1 are shown.

|  | Viral titre [TCID$_{50}$/ml] at 30° C. | Viral titre [TCID$_{50}$/ml] at 37° C. |
| --- | --- | --- |
| Flask a | 7.50E+07 | 3.20E+07 |
| Flask b | 1.30E+08 | 3.20E+07 |
| Mean value | 1.00E+08 | 3.20E+07 |

TABLE 2

In Table 2 values from experiment 2 are shown.

|  | Viral titre [TCID$_{50}$/ml] at 30° C. | Viral titre [TCID$_{50}$/ml] at 37° C. |
| --- | --- | --- |
| Flask a | 1.30E+08 | 3.20E+07 |
| Flask b | 1.30E+08 | 2.40E+07 |
| Mean value | 1.30E+08 | 2.70E+07 |

The data from the first 2 experiments are very promising that an increase in the yield of MVA can be achieved by decreasing the incubation temperature after infection. Therefore, it was decided to go ahead and try also other temperatures to find an optimal infection temperature. The used temperatures were 30, 33, 35 and 37° C. The results from this experiment are shown in Table 3 and FIG. 3.

Comparing the yields of 37° C. and lower infection temperatures (35, 33, 30° C.) showed a clear increase at lower temperatures. The best viral titre [TCID50/ml] was obtained in this experiment with an infection temperature of 30° C., which was 0.8 logs higher compared to 37° C.

TABLE 3

In Table 3 viral titres [TCID$_{50}$/ml] obtained at 30, 33, 35 and 37° C. are shown.

|  | Viral titre [TCID$_{50}$/ml] at 30° C. | Viral titre [TCID$_{50}$/ml] at 33° C. | Viral titre [TCID$_{50}$/ml] at 35° C. | Viral titre [TCID$_{50}$/ml] at 37° C. |
| --- | --- | --- | --- | --- |
| Flask a | 1.30E+08 | 5.60E+07 | 3.20E+07 | 3.20E+07 |
| Flask b | 1.30E+08 | 1.00E+08 | 7.50E+07 | 1.30E+07 |
| Mean value | 1.30E+08 | 7.50E+07 | 4.90E+07 | 2.10E+07 |

In the next experiment in stationary flasks even lower temperatures than 30° C. were tested to see if 30° C. is really the optimal temperature for multiplying of MVA in CEF cells. Therefore, 26, 28, 30 and 33° C. were used. The results from this experiment are shown in Table 4 and FIG. 4.

TABLE 4

In Table 4 viral titres [TCID$_{50}$/ml] obtained at 26, 28, 30 and 33° C. are shown.

|  | Viral titre [TCID$_{50}$/ml] at 26° C. | Viral titre [TCID$_{50}$/ml] at 28° C. | Viral titre [TCID$_{50}$/ml] at 30° C. | Viral titre [TCID$_{50}$/ml] at 33° C. |
| --- | --- | --- | --- | --- |
| Flask a | 3.20E+07 | 1.00E+08 | 4.20E+08 | 1.80E+08 |
| Flask b | 1.00E+08 | 1.80E+08 | 2.40E+08 | 1.00E+08 |
| Mean value | 5.60E+07 | 1.30E+08 | 3.20E+08 | 1.30E+08 |

The highest yield in this experiment was found at an incubation temperature after infection of 30° C. Comparing the data from the experiment before (4 temperatures between 30 and 37° C.) and this one, 30° C. was identified as the optimal temperature for the incubation after infection for the multiplying of MVA on CEF cells in stationary flasks.

Analysing the viral titers of the single temperatures from these two experiments, it became clear that incubation at 37° C. might even give the lowest virus yield out of the 6 used temperatures. The observed order for the yields at the used temperatures is the following:

30° C.>33° C./28° C.>35° C./26° C.>37° C.

Example 2

Effect of the Temperature on the Multiplication of Vacciniavirus Strain Elstree

In another approach Vaccinia virus strain Elstree was tested in addition to MVA-BN for temperature-dependance. MVA-BN and Elstree were multiplied on CEF-cells. For the experiment primary CEF-cells were seeded in stationary flasks with a seeding cell density of 2E+07 CEF cells/175 cm². Cells were seeded in culture media +4 mM L-Glutamine and 1% Antibiotics/Antimycotics. At day four after seeding a cell density of 5E+07 CEF-cells/175 cm² was assumed. The cells were infected with 0.1 $TCID_{50}$/cell MVA-BN by using RPMI w/o FCS and Elstree, respectively. The infection, followed by incubation for 72 h, was performed at 30° C. and 37° C. The experiment was performed in triplicates for each temperature. Virus replication was stopped by freezing stationary flasks at −20° C. This mixture was freeze/thawed another three times to mechanically release the virus from the cells.

Virus titers from every stationary flask were determined by titration according to SOP/MVA/04. As an acceptance criterion for titration results MVA F6 Standard with known titer was used as an internal control for each titration experiment. Results from the experiments were only taken when the values from MVA F6 Standard did not differ more than ±0.5 logs.

The results from the infection experiments are shown in table 5 and in FIG. 5.

The data of the experiment with MVA-BN show a clear increase in the virus yield at 30° C. compared to 37° C. (0.667 logs). In the experiments with Elstree an increase of 1.125 logs at 30° C. compared to 37° C. was found.

TABLE 5

In table 5 virus titers [$\log_{10}$ $TCID_{50}$/ml] obtained at 30 and 37° C. for MVA-BN and Vaccinia Virus strain Elstree are shown.

|  | MVA 30° C. | MVA 37° C. | Elstree 30° C. CEF cells | Elstree 37° C. CEF cells |
| --- | --- | --- | --- | --- |
| Flask a | 9.0 | 7.88 | 7.25 | 6.375 |
| Flask b | 8.0 | 8.0 | 8 | 6.5 |
| Flask c | 8.25 | 7.38 | 7.5 | 6.5 |
| Mean value | 8.42 | 7.75 | 7.583 | 6.458 |

What is claimed is:

1. A process of amplifying a Chordopoxvirus characterized in that the virus is propagated in culture media at a cultivation temperature below 37° C., wherein the chordopoxvirus is selected from Avipoxvirus and modified vaccinia virus Ankara (MVA).

2. Process according to claim 1, wherein the poxvirus is propagated in chicken embryo fibroblast cells.

3. Process according to claim 1, wherein the Chordopoxvirus is propagated at a cultivation temperature of about 26° C. to about 36° C.

4. Process of amplifying a Chordopoxvirus characterized in that the virus is propagated in chicken embryo fibroblasts at a cultivation temperature of 26° C. to 32° C.

5. Process according to claim 4, wherein the Chordopoxvirus is selected from the group consisting of Avipoxvirus and Orthopoxvirus.

6. Process according to claim 5, wherein the Orthopoxvirus is a vaccinia virus.

7. Process according to claim 6, wherein the vaccinia virus is selected from strain Elstree and modified vaccinia virus Ankara (MVA).

8. Process according to claim 1, wherein the Chordopoxvirus is propagated at a cultivation temperature of about 26° C. to 35° C.

9. Process according to claim 1, wherein the Chordopoxvirus is propagated at a cultivation temperature of about 30° C.

10. Process according to claim 1, wherein the virus propagation is performed for at least 24 hours.

11. Process according to claim 1, wherein the virus cultivation is performed for at least 2 to 3 days.

12. Process according to claim 1, wherein the Chordopoxvirus is a virus useful as a vaccine.

13. Process according to claim 1, wherein the process is performed in a stationary flask.

14. Process according to claim 1, wherein the pox virus is not a temperature sensitive mutant virus.

15. Process according to claim 1, wherein the pox-virus is not a temperature attenuated virus.

16. Process according to claim 1, wherein no lipids or surfactants are added to the culture media.

17. Process according to claim 1 wherein the modified vaccinia virus Ankara (MVA) is MVA-BN as deposited at ECACC under No. V00083008 or a derivative virus which shows the same temperature dependency as the deposited strain.

18. Process according to claim 1 wherein the Chordopoxvirus is propagated in avian cell culture.

19. Process according to claim 7 wherein the modified vaccinia virus Ankara (MVA) is MVA-BN as deposited at ECACC under No. V00083008 or a derivative virus which shows the same temperature dependency as the deposited strain.

20. Process according to claim 6 wherein the vaccinia virus is strain Elstree.

21. Process according to claim 4, wherein the Chordopoxvirus is propagated at a cultivation temperature of about 30° C.

22. Process according to claim 4, wherein the virus propagation is performed for at least 24 hours.

23. Process according to claim 4, wherein the virus cultivation is performed for at least 2 to 3 days.

24. Process according to claim 4, wherein the Chordopoxvirus is a virus useful as a vaccine.

25. Process according to claim 4, wherein the process is performed in a stationary flask.

26. Process according to claim 4, wherein the pox virus temperature sensitive mutant virus.

27. Process according to claim 4, wherein the pox-virus is not a temperature attenuated virus.

28. Process according to claim 4, wherein no lipids or surfactants are added to the culture media.

* * * * *